United States Patent [19]

Karim et al.

[11] 3,972,871

[45] Aug. 3, 1976

[54] 6β,17-DIHYDROXY-7α-(LOWER ALKOXY)CARBONYL-3-OXO-17α-PREGN-4-ENE-21-CARBOXYLIC ACID γ-LACTONES AND CONGENERS

[75] Inventors: Aziz Karim, Niles, Ill.; William J. Marsheck, Harbor Beach, Mich.; Richard M. Weier, Deerfield, Ill.

[73] Assignee: G. D. Searle & Co., Chicago, Ill.

[22] Filed: Sept. 22, 1975

[21] Appl. No.: 615,412

[52] U.S. Cl.................... 260/239.57; 260/397.1; 195/51 S
[51] Int. Cl.².................................. C07J 19/00
[58] Field of Search............... 260/239.57; /Machine Searched Steroids

[56] References Cited
UNITED STATES PATENTS
3,900,467   8/1975   Irmscher et al.................. 260/239.5

*Primary Examiner*—Elbert L. Roberts
*Attorney, Agent, or Firm*—Barbara L. Cowley

[57] ABSTRACT

The preparation and valuable biological properties - especially diuretic activity - of 6β,17-dihydroxy-7α-(lower alkoxy)carbonyl-3-oxo-17α-pregn-4-ene-21-carboxylic acid γ-lactones and the corresponding hydroxy acids and salts thereof are disclosed.

9 Claims, No Drawings

6β,17-DIHYDROXY-7α-(LOWER ALKOXY)CARBONYL-3-OXO-17α-PREGN-4-ENE-21-CARBOXYLIC ACID Γ-LACTONES AND CONGENERS

The present invention relates to 6β,17-dihydroxy-7α-(lower alkoxy)carbonyl-3-oxo-17α-pregn-4-ene-21-carboxylic acid γ-lactones and congeners. More particularly, this invention provides chemical compounds of the general formulas

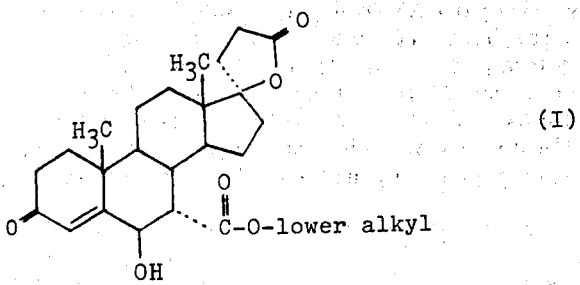

(I)

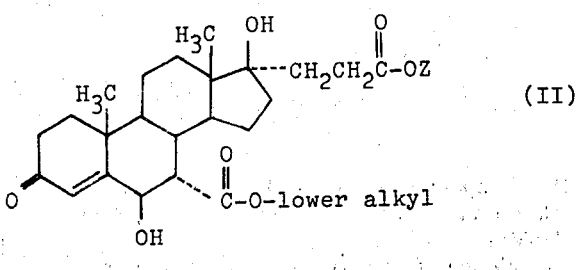

(II)

wherein Z represents hydrogen, alkali metal, or alkaline-earth metal/2. Preferred compounds of formula (II) are those compounds wherein the Z is alkali metal or alkaline-earth metal/2.

Those skilled in the art will recognize that the term "alkaline-earth metal/2" is dictated by the fact that such metals are divalent, whereas the other substituents represented by Z are monovalent; and when, for example, Z represents Ca/2 in formula (II), the contemplated salts are more conventionally depicted thus

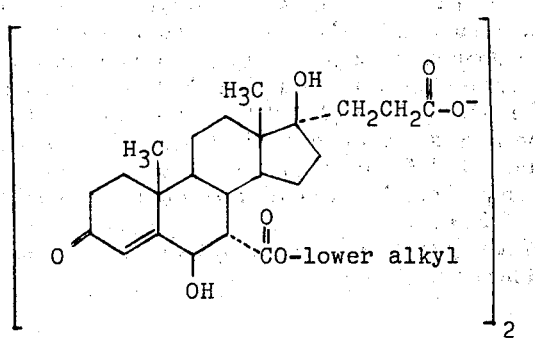

The lower alkyl radicals contain from 1 to 7 carbon atoms. These lower alkyl radicals are exemplified by methyl, ethyl, propyl, isopropyl, butyl, isobutyl, sec.-butyl, tert.-butyl, pentyl, neopentyl, hexyl, isohexyl, heptyl, and like monovalent, saturated acyclic straight- or branched-chain hydrocarbon groupings of the empirical formula

wherein n represents an integer less than 8.

Preferred alkali metals and alkaline-earth metals encompassed by the Z term include potassium, sodium, lithium, magnesium, and calcium.

Equivalent to the compounds of formulas (I) and (II) for the purposes of this invention are solvates thereof in which biologically insignificant amounts of solvent are present.

The foregoing compounds are useful by reason of their valuable biological properties. Thus, for example, they are useful diuretics. They reverse the effect of desoxycorticosterone acetate (DCA) on urinary sodium and potassium.

The capacity of the instant compounds to reverse the renal electrolyte effects is evident from the results of a standardized test for this property carried out in rats substantially as described by C. M. Kagawa in Chapter 34 of volume II of "Evaluation of Drug Activities: Pharmacometrics," by D. R. Laurence and A. L. Bacharach. Details of such testing are described in U.S. Pat. No. 3,422,096.

A representative compound of this invention which is particularly active in this standardized test is 6β,17-dihydroxy-7α-methoxycarbonyl-3-oxo-17α-pregn-4-ene-21-carboxylic acid γ-lactone.

Those skilled in the art will recognize that observations of activity in standardized tests for particular biological effects are fundamental to the development of valuable new drug products, both veterinary and human.

The compounds of formula (I) are conveniently prepared from a compound of the formula

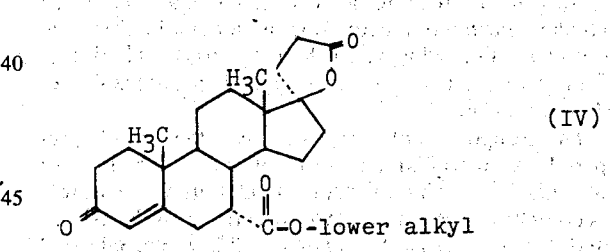

(IV)

wherein the lower alkyl group contains 1 to 7 carbon atoms, by preparing the corresponding dienol ether, and oxidizing this dienol ether with a suitable peroxyacid in an aqueous organic solvent.

This oxidation is preferably carried out by the method described by Kirk and Wiles, Chem. Comm., 5 18, 1015 (1970). A particularly preferred peroxy-acid is m-chloroperbenzoic acid which has been buffered by first being half-neutralized with sodium hydroxide. Other peroxy acids useful in the present invention include perbenzoic acid and monoperphthalic acid. Suitable solvents include, but are not limited to, aqueous dioxane and aqueous tetrahydrofuran, a particularly preferred solvent being aqueous dioxane.

The dienol ether intermediates are conveniently prepared by condensing a compound of formula (IV) with triethylorthoformate and ethanol in the presence of a catalytic amount of acid. This reaction may be conducted in the presence or absence of a solvent. When a solvent is used, suitable solvents include, but are not limited to, benzene, toluene, dioxane and dimethylformamide. Although triethylorthoformate and ethanol are preferred reagents for the preparation of the dienol ethers, other etherifying reagents such as trimethylorthoformate and methanol, or acetone dimethyl ketal (2,2-dimethoxypropane), may be used. Suitable catalytic acids include, but are not limited to, p-toluenesulfonic acid, perchloric acid and hydrochloric acid, a particularly preferred acid being p-toluenesulfonic acid.

Preparation of the compounds of formula (II) wherein Z is an alkali metal is accomplished by warming the 6β,17-dihydroxy-7α-(lower alkoxy)carbonyl-3-oxo-17α-pregn-4-ene-21-carboxylic acid γ-lactone in slightly less than one equivalent of an alkali metal hydroxide in methanol. Brief contact of the resulting alkali metal 6β,17-dihydroxy-7α-(lower alkoxy)carbonyl-3-oxo-17α-pregn-4-ene-21-carboxylate with one equivalent of very dilute hydrochloric acid yields the corresponding 6β,17-dihydroxy-7α-(lower alkoxy)carbonyl-3-oxo-17α-pregn-4-ene-21-carboxylic acid. Contacting one of the latter acids with one equivalent of an alkaline-earth metal hydroxide in methanol affords the corresponding alkaline-earth metal 6β,17-dihydroxy-7α-(lower alkoxy)carbonyl-3-oxo-17α-pregna-4-ene-21-carboxylate.

The compounds of formula (I) are alternatively prepared by microbial oxidation of the compounds of formula (IV). This microbial oxidation is preferably accomplished by the method described by Marsheck and Karim, *Applied Microbiology*, 25, 4, pp. 647-649 (1973), utilizing *Chaetomium cochloids* QM624 (Available from the Quartermaster Culture Collection, Quartermaster Research and Engineering Command, U.S. Army, Natick, Mass.).

The starting materials of formula (IV) and methods for their preparation are described in U.S. Pat. No. 3,787,396.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees centigrade (°C.), and relative amounts in parts by weight except as otherwise noted.

EXAMPLE 1

6β,17-DIHYDROXY-7α-METHOXYCARBONYL-3-OXO-17α-PREGN-4-ENE-CARBOXYLIC ACID γ-LACTONE.

To a stirred slurry of 1.43 parts of 17-hydroxy-7α-methoxycarbonyl-3-oxo-17α-pregn-4-ene-21-carboxylic acid γ-lactone in 1.3 parts of triethyl orthoformate and 2.4 parts of ethanol is added 0.1 part of solid p-toluenesulfonic acid. The mixture is stirred for about 15 minutes or until it becomes homogeneous. Then, excess anhydrous sodium acetate (0.4 part) and 0.2 part of pyridine is added. The resulting mixture is concentrated under reduced pressure and the residue treated with ethyl acetate. The insoluble material is filtered and the filtrate concentrated under reduced pressure to give a viscous yellow oil. After drying in vacuo for two hours, the residue is dissolved in a minimum amount of methanol containing a trace of pyridine. Refrigeration for about 18 hours yields crystals of 3-ethoxy-17-hydroxy-7α-methoxycarbonyl-17α-pregna-3,5-diene-21-carboxylic acid γ-lactone, melting at about 90°–93° and represented by the following structural formula

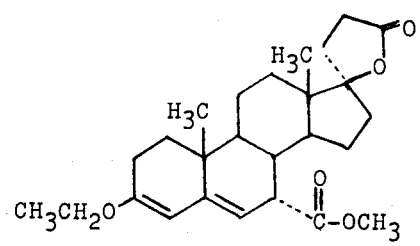

This compound exhibits an $[\alpha]_D = -10°$ (c = 0.125, chloroform) and $\lambda_{max} = 236$ mμ in methanol (ε = 15,680).

A solution of 4.56 parts of 81% m-chloroperbenzoic acid in 30 parts by volume of a 10% aqueous dioxane is half-neutralized with 13.69 parts by volume of a 0.98 N sodium hydroxide solution and cooled to 0°C. The solution is then added in portions over a 2.5 hour period to a stirred solution of 6.98 parts of 3-ethoxy-17-hydroxy-7α-methoxycarbonyl-17α-pregna-3,5-diene-21-carboxylic acid γ-lactone in 70 parts by volume of a 10% aqueous dioxane solution. The reaction mixture is stirred at room temperature for about 18 hours, poured into ice water, and then extracted four times with portions of methylene chloride. The organic layer is separated, extracted once with water and dried over anhydrous sodium sulfate. The residue is purified by chromatography on silica gel using ethyl acetate-benzene mixtures as eluants. The desired product is obtained on elution with 50:50 ethyl acetate-benzene. Recrystallization from a mixture of ethyl acetate and n-hexane affords 6β,17-dihydroxy-7α-methoxycarbonyl-3 -oxo-17α-pregn-4-ene-21-carboxylic acid γ-lactone, melting at 203°–205°C.

This compound is represented by the following structural formula:

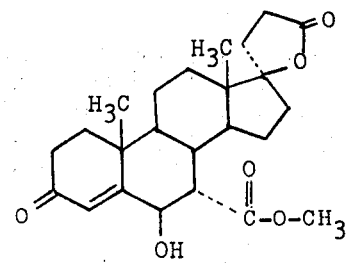

EXAMPLE 2

6β,17-DIHYDROXY-7α-ISOPROPOXYCARBO-NYL-3-OXO-17α-PREGNENE-21-CARBOXYLIC ACID γ-LACTONE 0.2 part of p-toluenesulfonic acid is added to a stirred solution of 4.85 parts of 17-hydroxy-7α-isopropoxycarbonyl-3-oxo-17α-pregn-4-ene-21-carboxylic acid γ-lactone in 4.45 parts of ethanol. The mixture is stirred for 20 minutes and then 5.0 parts of sodium acetate and 0.05 part of pyridine are added. The solvent is removed under reduced pressure. The residue is stirred with ethyl acetate and filtered. The filtrate is concentrated under reduced pressure and the residue dried in vacuo to afford 3-ethoxy-17-hydroxy-7α-isopropoxycarbonyl-17α-pregna-3,5-diene-21-carboxylic acid γ-lactone.

To a cooled solution of 2.0 parts m-chloroperbenzoic acid in 20 parts of dioxane is added 5.9 parts by volume of 0.98 N sodium hydroxide solution. This solution is cooled to 0°C. and added portionwise over a period of 2.5 hours to a solution of 5 parts of 3-ethoxy-17-hydroxy-7α-isopropoxycarbonyl-17α-pregna-3,5-diene-21-carboxylic acid γ-lactone in 50 parts of dioxane. After completion of this addition, a further 0.5 parts of m-chloroperbenzoic acid in 5 parts of dioxane is half neutralized by the addition of 1.2 parts by volume of a 0.98 N sodium hydroxide solution and added to the reaction mixture. The reaction is then stirred at room temperature for 5 hours. A final addition of a solution of 0.5 parts of m-chloroperbenzoic acid in 5 parts of dioxane that is half neutralized by 1.2 parts by volume of 0.98 N sodium hydroxide is made over a two hour period. The reaction mixture is then concentrated under reduced pressure and the residue dissolved in methylene chloride, washed with water, and dried over anhydrous sodium sulfate. The crude product is purified by chromatography on silica gel. Recrystallization from ethyl acetate and n-hexane of the product eluted with 30:70 ethyl acetate-benzene affords 6β,17-dihydroxy-7α-isopropoxycarbonyl-3-oxo-17α-pregn-4-ene-21-carboxylic acid γ-lactone. This product melts at 188°–189°C. and is represented by the following structural formula.

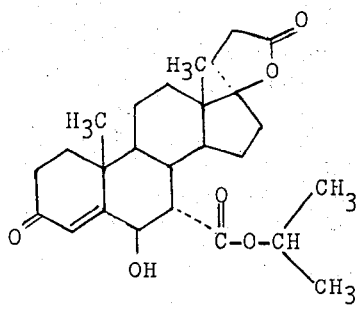

EXAMPLE 3

6β,17-DIHYDROXY-7α-n-BUTOXYCARBONYL-3-OXO-17α-PREGN-4-ENE-21-CARBOXYLIC ACID γ-LACTONE

Substitution of an equivalent quantity of 7α-n-butoxycarbonyl-17-hydroxy-3-oxo-17α-pregn-4-ene-21-carboxylic acid γ-lactone in the procedure of Example 1 affords 6β,17-dihydroxy-7α-n-butoxycarbonyl-3-oxo-17α-pregn-4-ene-21-carboxylic acid γ-lactone. This compound displays an $[\alpha]_D = -10°$ (1.029) in chloroform, and a $\lambda_{max}$ in methanol at 237 mμ with an $\epsilon$=19,200.

EXAMPLE 4

POTASSIUM 6β,17-DIHYDROXY-7α-METHOXYCARBONYL-3-OXO-17α-PREGN-4-ENE-21-CARBOXYLATE

A solution of 10 parts of 6β,17-dihydroxy-7α-methoxycarbonyl-3-oxo-17α-pregn-4-ene-21-carboxylic acid γ-lactone and 22 parts of aqueous 4% potassium hydroxide in 300 parts of methanol is protected by a nitrogen atmosphere. The solution is stirred at room temperature for about 18 hours and then heated at 40°–50°C. for 20 minutes. The solvent is then removed by vacuum distillation and the residue dried by azeotroping with ethanol. The resulting oil is treated with ethyl acetate to give a white solid. This solid is filtered and dried to give potassium 6β,17-dihydroxy-7α-methoxycarbonyl-3-oxo-17α-pregn-4-ene-21-carboxylate. This compound may be represented by the following structural formula.

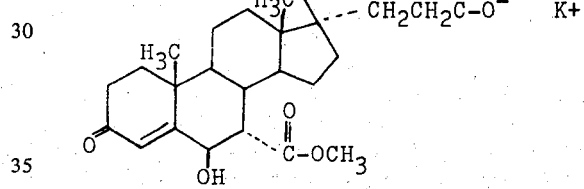

EXAMPLE 5

SODIUM 6β,17-DIHYDROXY-7α-ISOPROPOXYCARBO-NYL-3-OXO-17α-PREGN-4-ENE-21-CARBOXYLATE

Substitution of an equivalent quantity of 6β,17-dihydroxy-7α-isopropoxycarbonyl-3-oxo-17α-pregn-4-ene-21-carboxylic acid γ-lactone for the 6β,17-dihydroxy-7α-methoxycarbonyl-3-oxo-17α-pregn-4-ene-21-carboxylic acid γ-lactone of Example 4 and aqueous 5% sodium hydroxide for the aqueous 4% potassium hydroxide used therein, and repetition of the procedure detailed therein affords as a white solid, sodium 6β,17-dihydroxy-7α-isopropoxycarbonyl-3-oxo-17α-pregn-4-ene-21-carboxylate.

EXAMPLE 6

6β,17-DIHYDROXY-7α-METHOXYCARBONYL-3-OXO-17α-PREGN-4-ENE-21-CARBOXYLIC ACID

To a solution of 1 part of potassium 6β,17-dihydroxy-7α-methoxycarbonyl-3-oxo-17α-pregn-4-ene-21-carboxylate in 70 parts of water is added 20 parts of 5% hydrochloric acid. The resultant precipitate is filtered off, washed with water, and dried in air. The material thus isolated is 6β,17-dihydroxy-7α-methoxycarbonyl-3-oxo-17α-pregn-4-ene-21-carboxylic acid. The formula of this compound is represented as follows.

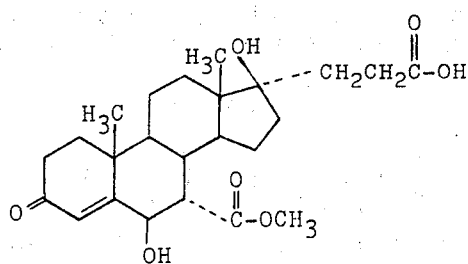

EXAMPLE 7

CALCIUM BIS[6β,17-DIHYDROXY-7α-METHOXYCARBONYL-3-OXO-17α-PREGN-4-ENE-21-CARBOXYLATE]

A mixture of 10 parts of 6β,17-dihydroxy-7α-methoxycarbonyl-3-oxo-17α-pregn-4-ene-21-carboxylic acid, 0.9 part of calcium hydroxide and 200 parts of methanol is stirred at 40°C. under nitrogen for 2 hours. Solvent is then removed by vacuum distillation, and the residue recrystallized from ethyl acetate. The product thus isolated is calcium bis[6β,17-dihydroxy-7α-methoxycarbonyl-3-oxo-17α-pregn-4-ene-21-carboxylate].

EXAMPLE 8

A 72-hour shaken flask culture of *Chaetomium cochlioides* is allowed to sporulate for 3 days standing at room temperature. The culture is then diluted with 300 parts of sterile water and added to a 30 liter fermentor (Fermentation Design, Inc.) charged with a sterilized medium consisting of 230 parts of 10% soy peptone, 57.5 parts of 2.5% yeast extract (Amberex 1003) and 230 parts of 10% dextrose. The air flow rate is set at 10 liters/minute, agitation at 300 revolutions/minute, pressure at 2 lbs., and the temperature maintained at 27°C. After 2.5 hours, silicon antifoam compound (Mazer Chemicals, Inc.) and 10 parts of 17-hydroxy-7α-methoxycarbonyl-3-oxo-17α-pregn-4-ene-21-carboxylic acid γ-lactone dissolved in 59 parts of acetone is added.

After 22 hours of fermentation, the contents of the fermentator are extracted with methylene chloride. The solvent is removed from the methylene chloride extract under reduced pressure and the residue chromatographed on a 3-inch column of 1100 parts of silica gel. The column is eluted with mixtures containing increasing amounts of ethyl acetate in methylene chloride. The desired product is obtained in the 100% ethyl acetate fraction. Re-chromatography of this product using a 15 inch column of 120 parts of silica gel and the same elution solution, gave the desired product in the 15–20% ethyl acetate fractions. Crystallization from ethyl ether and drying at 80°C. in vacuo affords 6β,17-dihydroxy-7α-methoxycarbonyl-3-oxo-17α-pregn-4-ene-21-carboxylic acid γ-lactone, identical to the product of Example 1.

What is claimed is:

1. A compound of the general formula

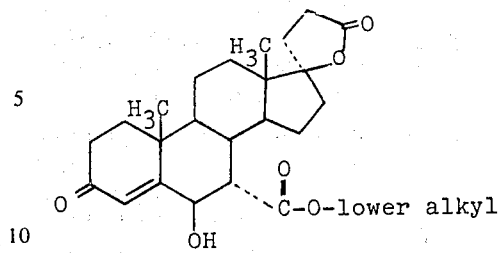

(I)

or

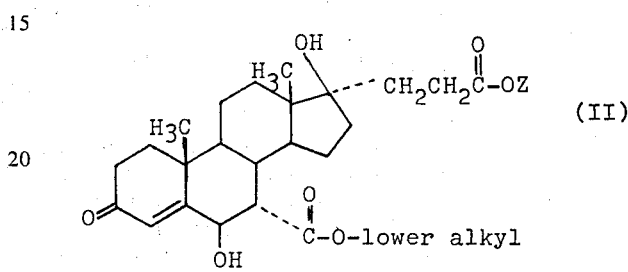

(II)

wherein the lower alkyl group contains 1 to 7 carbon atoms, and Z represents hydrogen, alkali metal, or alkaline-earth metal/2.

2. A compound according to claim 1 having the formula:

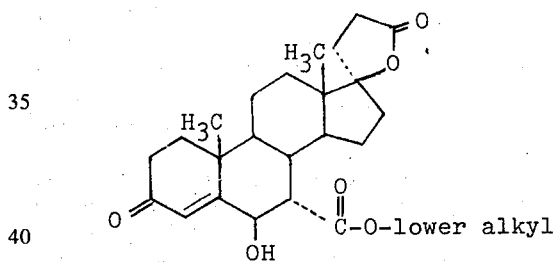

wherein the lower alkyl group contains 1–7 carbon atoms.

3. A compound according to claim 1 which is 6β,17-dihydroxy-7α-methoxycarbonyl-3-oxo-17α-pregn-4-ene-21-carboxylic acid γ-lactone.

4. A compound according to claim 1 which is 6β,17-dihydroxy-7α-isopropoxycarbonyl-3-oxo-17α-pregn-4-ene-21-carboxylic acid γ-lactone.

5. A compound according to claim 1 which is 6β,17-dihydroxy-7α-n-butoxycarbonyl-3-oxo-17α-pregn-4-ene-21-carboxylic acid γ-lactone.

6. A compound according to claim 1 having the formula

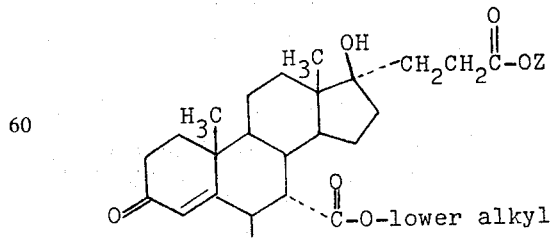

wherein the lower alkyl group contains from 1 to 7 carbon atoms and Z represents hydrogen, alkali metal, or alkaline-earth metal/2.

7. A compound according to claim 1 which is potassium 6β,17-dihydroxy-7α-methoxycarbonyl-3-oxo-17α-pregn-4-ene-21-carboxylate.

8. A compound according to claim 1 which is sodium 6β,17-dihydroxy-7α-isopropoxycarbonyl-3-oxo-17α-pregn-4-ene-21-carboxylate.

9. A compound according to claim 1 which is calcium bis[6β,17-dihydroxy-7α-methoxycarbonyl-3-oxo-17α-pregn-4-ene-21-carboxylate].

* * * * *